(12) United States Patent
Kidmose et al.

(10) Patent No.: US 10,413,208 B2
(45) Date of Patent: Sep. 17, 2019

(54) EEG MONITORING SYSTEM AND METHOD OF MONITORING AN EEG

(75) Inventors: Preben Kidmose, Marslet (DK); Soren Erik Westermann, Humlebak (DK)

(73) Assignee: Widex A/S, Lynge (DK)

( * ) Notice: Subject to any disclaimer, the term of this patent is extended or adjusted under 35 U.S.C. 154(b) by 908 days.

(21) Appl. No.: 13/335,901

(22) Filed: Dec. 22, 2011

(65) Prior Publication Data
US 2012/0123290 A1     May 17, 2012

Related U.S. Application Data

(63) Continuation-in-part of application No. PCT/DK2009/050148, filed on Jun. 26, 2009.

(51) Int. Cl.
*A61B 5/0476* (2006.01)
*A61B 5/04* (2006.01)
*A61B 5/00* (2006.01)

(52) U.S. Cl.
CPC .......... *A61B 5/0476* (2013.01); *A61B 5/6815* (2013.01); *A61B 5/6838* (2013.01); *A61B 5/0031* (2013.01); *A61B 5/4094* (2013.01); *A61B 5/7264* (2013.01)

(58) Field of Classification Search
USPC ................................................. 600/544, 545
See application file for complete search history.

(56) References Cited

U.S. PATENT DOCUMENTS

| | | | |
|---|---|---|---|
| 6,354,299 B1 | 3/2002 | Fischell et al. | |
| 6,594,524 B2 * | 7/2003 | Esteller | A61B 5/0482 600/544 |
| 2003/0073917 A1 * | 4/2003 | Echauz | A61B 5/0476 600/510 |
| 2004/0267152 A1 * | 12/2004 | Pineda | 600/544 |
| 2006/0094972 A1 * | 5/2006 | Drew | 600/523 |
| 2007/0149952 A1 | 6/2007 | Bland et al. | |
| 2007/0276279 A1 * | 11/2007 | Echauz | A61B 5/0476 600/544 |
| 2008/0183096 A1 * | 7/2008 | Snyder | G06K 9/00496 600/545 |

(Continued)

FOREIGN PATENT DOCUMENTS

| | | |
|---|---|---|
| JP | 2004-350870 A | 12/2004 |
| KR | 10-2008-0096855 A | 11/2008 |

(Continued)

OTHER PUBLICATIONS

Japanese Office Action for Japanese Patent Application No. 2012-515355 dated Jun. 4, 2013 with English translation.

(Continued)

*Primary Examiner* — Etsub D Berhanu
(74) *Attorney, Agent, or Firm* — Sughrue Mion, PLLC

(57) ABSTRACT

An EEG monitoring system (2) adapted to be carried continuously by a person to be monitored comprises electrodes for measuring at least one EEG signal from the person carrying the EEG monitoring system (2). The system also comprises signal processing means adapted to receive, process and analyze the EEG signal. Furthermore the system comprises data logging means adapted to log data relating to said EEG signal and a memory for storing said data relating to said EEG signal. A method of using the monitoring system is also provided.

20 Claims, 6 Drawing Sheets

(56) References Cited

U.S. PATENT DOCUMENTS

Figure 1:
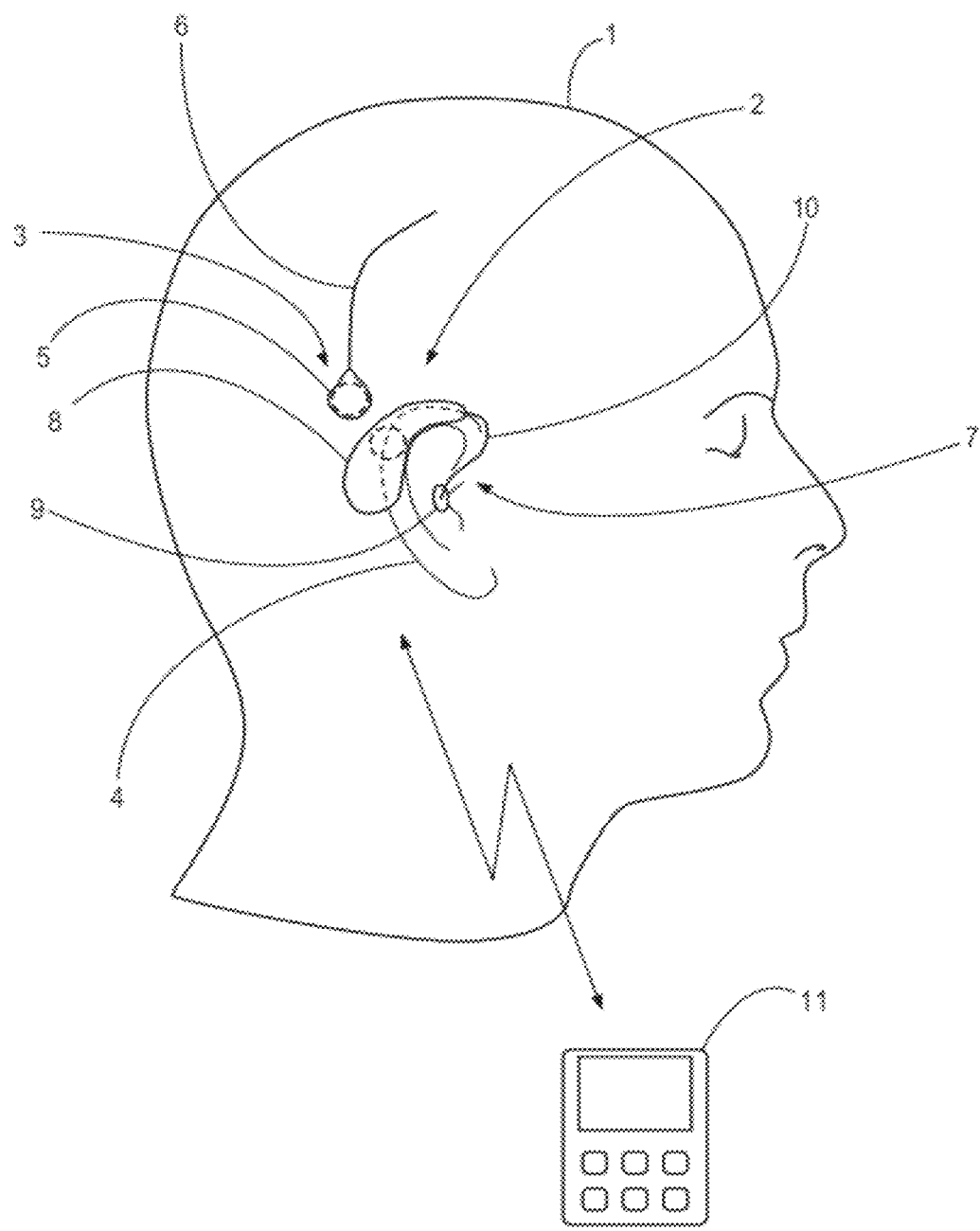

2009/0171168 A1* 7/2009 Leyde .................... A61B 5/048
600/301

FOREIGN PATENT DOCUMENTS

| WO | 02/100267 A1 | 12/2002 |
| WO | WO 2006066577 A1 | 6/2006 |
| WO | WO 2007144307 A2 * | 12/2007 |
| WO | WO 2007144307 A2 | 12/2007 |

OTHER PUBLICATIONS

Korean Office Action for Korean Patent Application No. 10-2011-7031083 dated Jun. 11, 2013 with English translation.
Bendtson et al, "Nocturnal electroencephalogram registrations in type 1 insulin-dependent diabetic patients with hypoglycaemia" Diabetologia, Springer, Berlin, DE, vol. 34, No. 10, Jan. 1, 1991, pp. 750-756, XP002997592.
International Search Report for PCT/DK2009/050148 dated Sep. 23, 2009.
Sarimari Tupola et al, "Abnormal electroencephalogram at diagnosis of insulin-dependent diabetes mellitus may predict severe symptoms of hyploglycemia in children" Journal of Pediatrics, Mosby-Year Book, St. Louis, MO US vol. 133, No. 6 Dec. 1, 1998 pp. 792-794 XP005692576.

* cited by examiner

EEG MONITORING SYSTEM AND METHOD OF MONITORING AN EEG

The present application is a continuation-in-part of application PCT/DK2009/050148, filed on Jun. 26, 2009, in Denmark and published as WO2010149158 A1.

BACKGROUND OF THE INVENTION

1. Field of the Invention

The present invention relates to monitoring EEG. The invention specifically relates to an EEG monitoring system adapted to be carried continuously by a person to be monitored. The invention furthermore relates to a method of monitoring an EEG.

EEG is the commonly used abbreviation for Electro EncephaloGram. EEG monitoring is generally speaking a method of electrically monitoring brain activity of a person. Systems for monitoring EEGs have been known for many years. However with the general technological development, EEG monitoring systems, which may be carried or worn continuously by a person to be monitored, have been devised.

2. The Prior Art

WO-A1-2006/066577 discloses a system for continued wearing by a person suffering from diabetes, where blood sugar levels are monitored in order to warn against hypoglycaemic attacks. Low blood sugar levels have severe influences on the brain activity, and too low blood sugar levels may lead to unconsciousness and even death. The system disclosed in WO-A1-2006/066577 is a fully implanted subcutaneous system. The implanted electrodes are via electrical leads connected to a monitoring device capable of detecting the brainwaves characteristic for an imminent hypoglycaemic attack, and of issuing a warning in the form of a vibration of the subcutaneous monitoring device. In WO-A1-2006/066577 it is furthermore suggested that the implant may wirelessly communicate with an external unit, which may contain the more power demanding parts of the electronics, so as to obtain a long battery service life of the implanted subcutaneous parts. This will also allow an acoustic warning. In order to detect an imminent hypoglycaemic attack, the system of WO-A1-2006/066577 looks at the frequencies and amplitudes of the brainwaves, which change prior to a hypoglycaemic attack as explained in WO-A1-2006/066577, which is incorporated herein by reference, the brainwaves going into a phase with waveform patterns with higher amplitudes and lower frequencies. It is suggested to use classifiers such as Bayesian classifiers, neural networks, or logistic regression, but WO-A1-2006/066577 does not disclose any details on how. Finally, WO-A1-2006/066577 suggests the build-in of dynamic adaptation of the signal processing algorithms, so as to continuously adapt these to the individual carrying the system. Also in this respect the document is silent about any way of achieving such dynamic adaptation.

SUMMARY OF THE INVENTION

Based on this prior art it is a feature of the present invention to provide an improved system. In this it is inter alia a feature to present a system and a method for providing the dynamic adaptation referred to above.

The invention, in a first aspect, provides a portable EEG monitoring system, said system comprising electrodes for measuring at least one EEG signal from the person carrying the EEG monitoring system, signal processing means adapted to receive, process and analyze at least a part of said EEG signal, wherein said signal processing means comprises a feature extractor for extracting a feature vector from said EEG signal, a classifier adapted for monitoring said feature vector for identifying an event and outputting an event signal to an event integrator adapted to integrate the event signals over time, in order to produce an event level signal, data logging means adapted to log data relating to said EEG signal and to log at least one feature vector extracted from said EEG signal, and a memory for storing said data relating to said EEG signal.

The invention, in a second aspect, provides a method for EEG monitoring using a portable EEG measuring system, said method comprising measuring at least one EEG signal from the person carrying the EEG monitoring system, receiving, processing and analyzing at least a part of said EEG signal using a signal processing means, said signal processing comprising the extraction of a feature vector from said EEG signal using a feature extractor, monitoring said feature vector, identifying an event using a classifier and outputting an event signal to an event integrator and producing an event level signal by integrating event signals over time using said event integrator, logging data relating to said EEG signal using a data logging means, at least one feature vector extracted from said EEG signal being logged in a data logging means, and storing said data relating to said EEG signal in a memory.

By logging data it becomes possible to carry out extensive evaluation of the data, in turn allowing a better analysis, better detection of predetermined events and better understanding of the relation between an individual's brain waves and imminent events, such as hypoglycaemic or epileptic seizures, as well as the possibility of making individual adjustments.

According to a preferred embodiment of said first aspect of the invention, said signal processing means comprises a feature extractor for extracting a feature vector from said EEG signal. Using a feature extractor allows a substantial reduction in the original amount of information of an EEG signal to be considered in an evaluation process where content of the signal is to be classified.

According to a further preferred embodiment of said first aspect of the invention, said analysing means comprises an event classifier for detecting predetermined events based on said EEG signal. Using an event classifier is an efficient way of distinguishing between the important events and immaterial events.

According to yet a further embodiment of said first aspect of the invention, said logging means is adapted to log information about a number of events, such as their time of occurrence. Logging a number of events moreover is an efficient way of providing basis for a decision such as an alarm depending on the occurrence of the important events. Moreover it substantially reduces the information to be stored, as compared to e.g. the fully sampled EEG signal.

According to another preferred embodiment of said first aspect of the invention, the data logging means is adapted to log at least one feature vector, extracted from said EEG signal. Logging only the feature vector entails a substantial savings in storage space, which is important in a small device to be worn behind the ear.

According to yet another preferred embodiment of said first aspect of the invention, the data logging means is adapted to log the waveform of the EEG signal. Keeping the full information of the waveform of the signal is preferable where storage considerations are of less importance.

According to an especially preferred embodiment of said first aspect of the invention, means are provided for detecting an abnormal brain condition based on the detected predetermined events, and initiating an alarm based on said detection of the abnormal brain condition.

According to a further preferred embodiment of said first aspect of the invention, the data logged by said data logging means is stored in said memory, upon detection of said abnormal brain condition. This allows the saving of information pertaining to the period leading up to the alarm, to be stored for further analysis.

Embodiments of the method according to the second aspect of the invention generally provide the same advantages as the embodiments according to the first aspect.

BRIEF DESCRIPTION OF THE INVENTION

Figure 2:
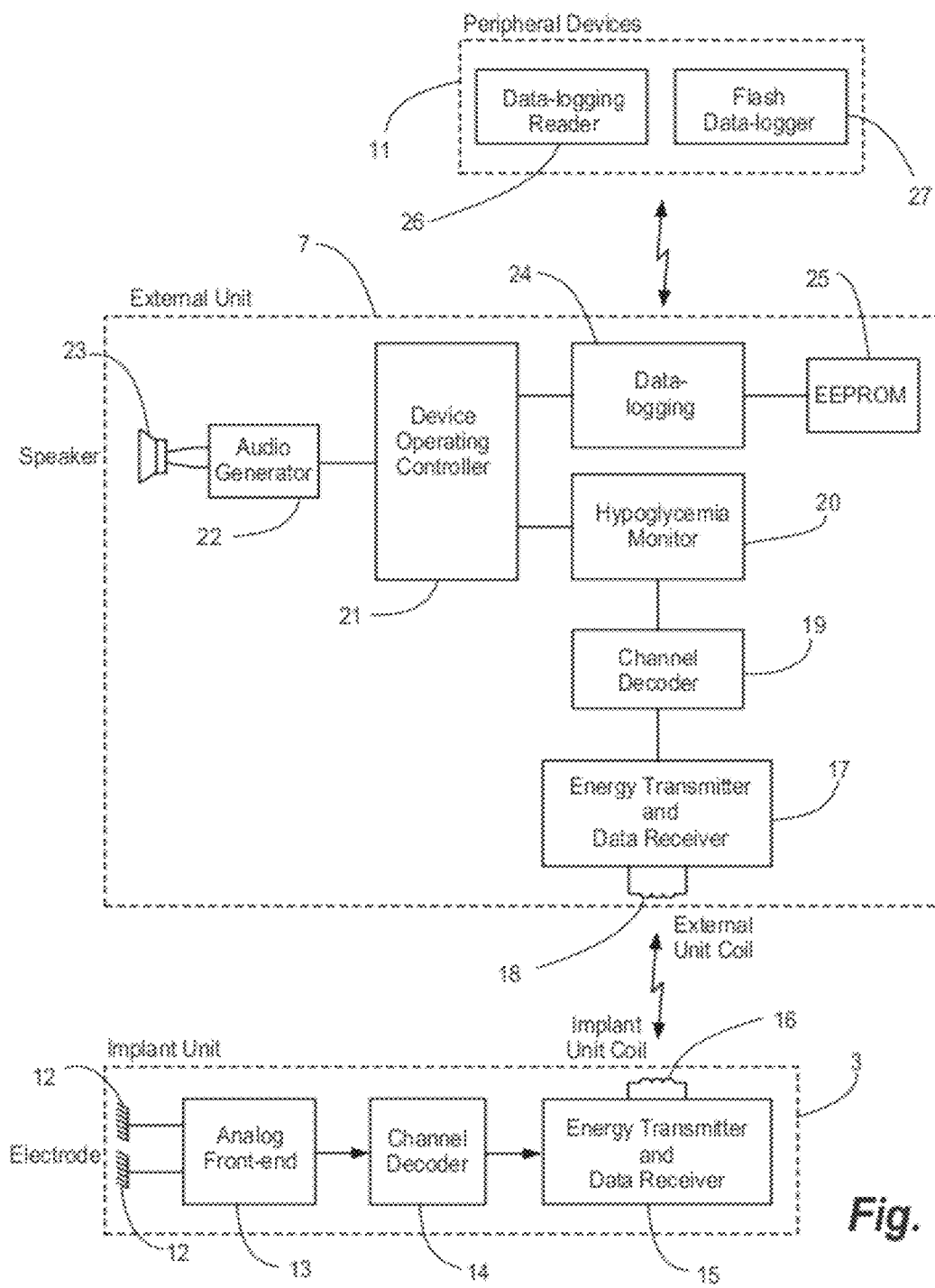
Figure 3:
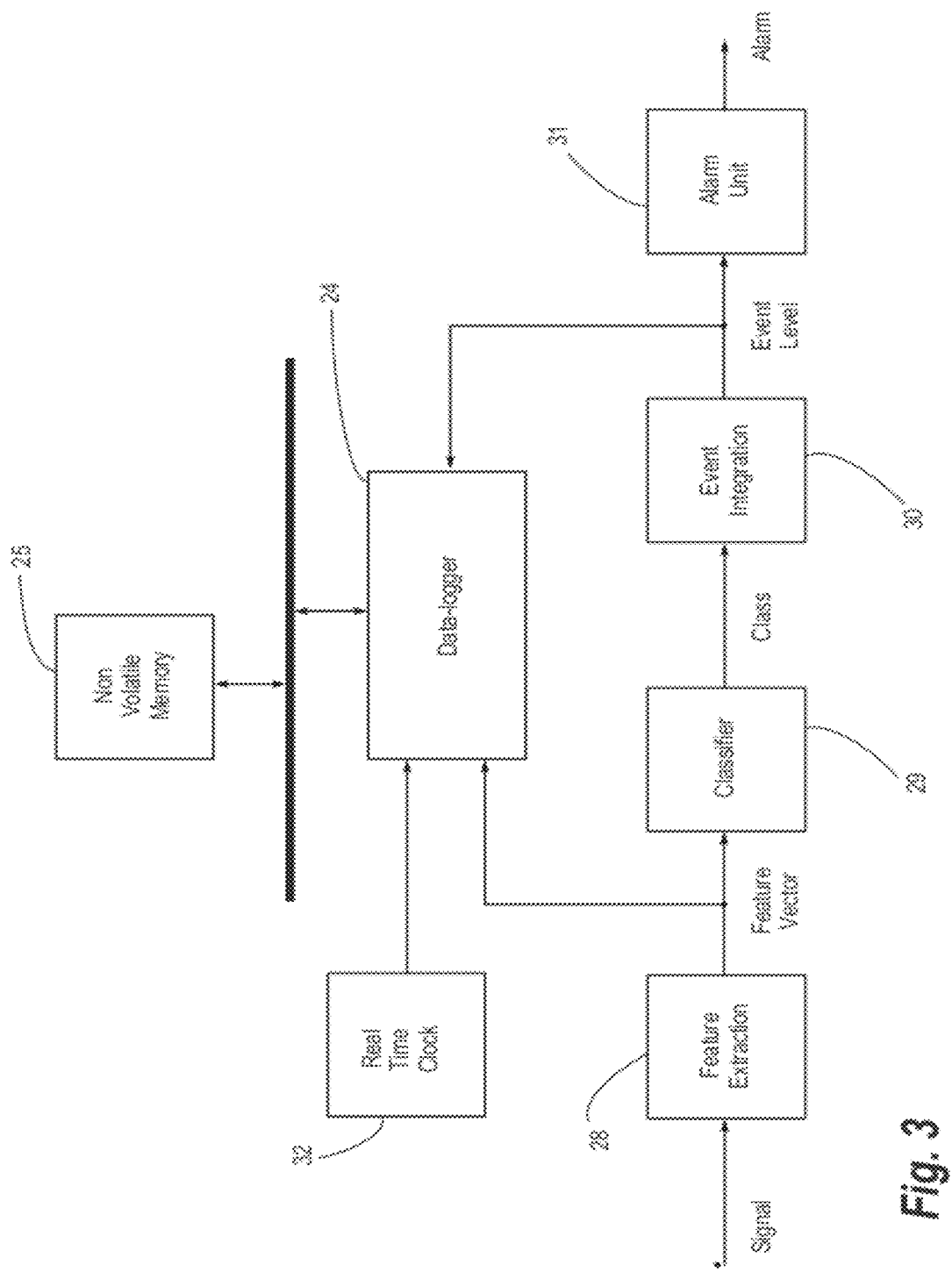
Figure 4:
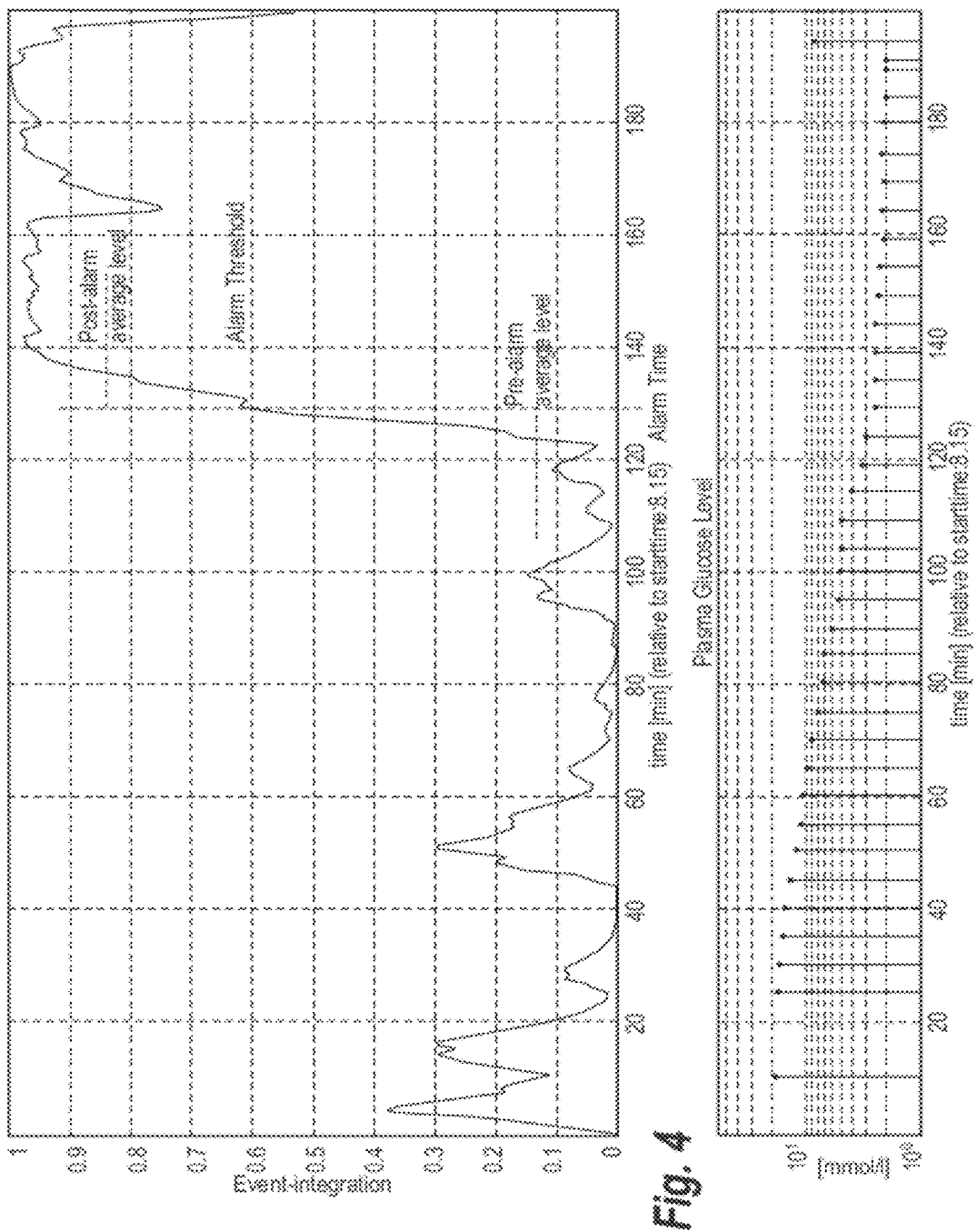
Figure 5:
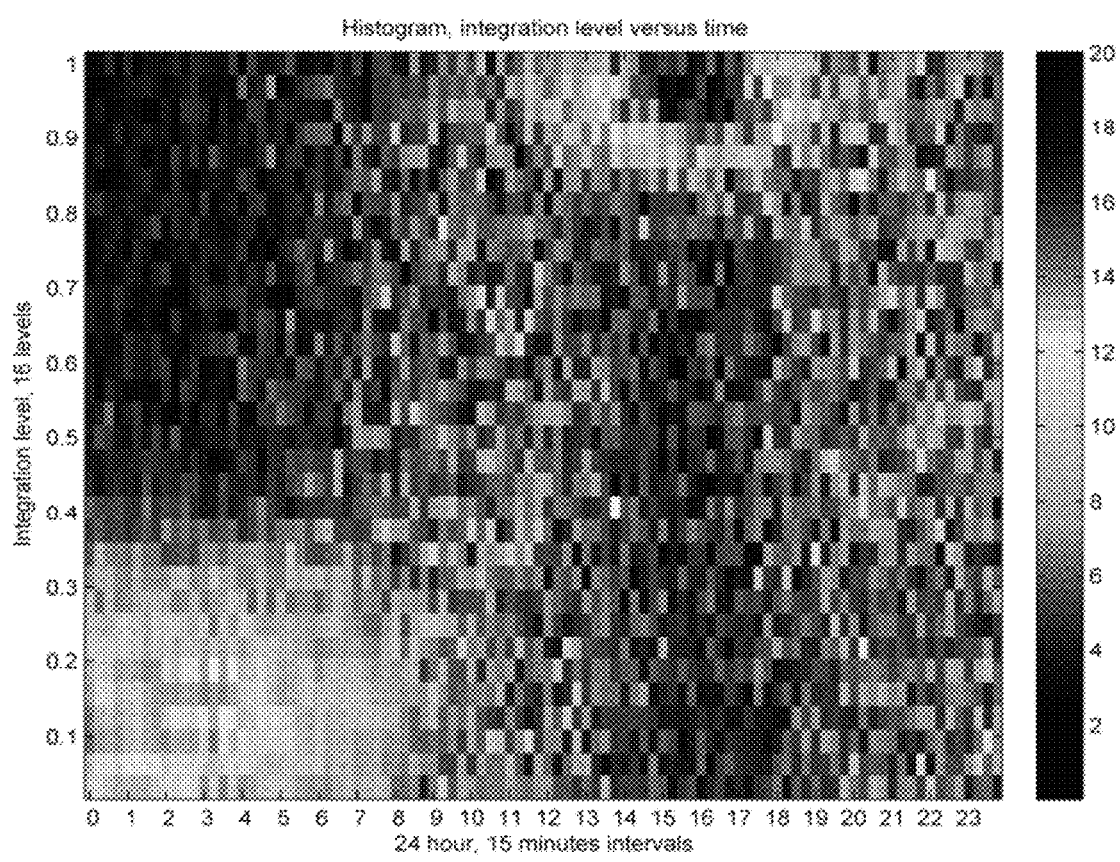
Figure 6:
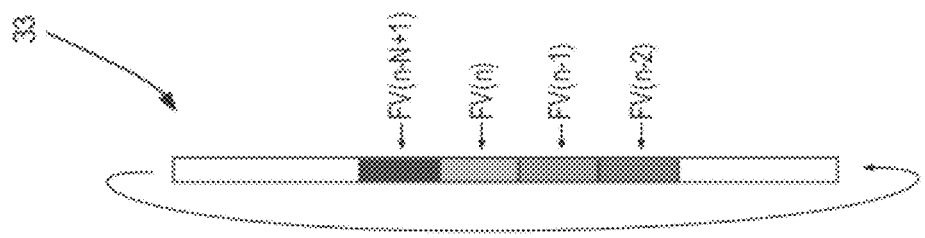
Figure 7:
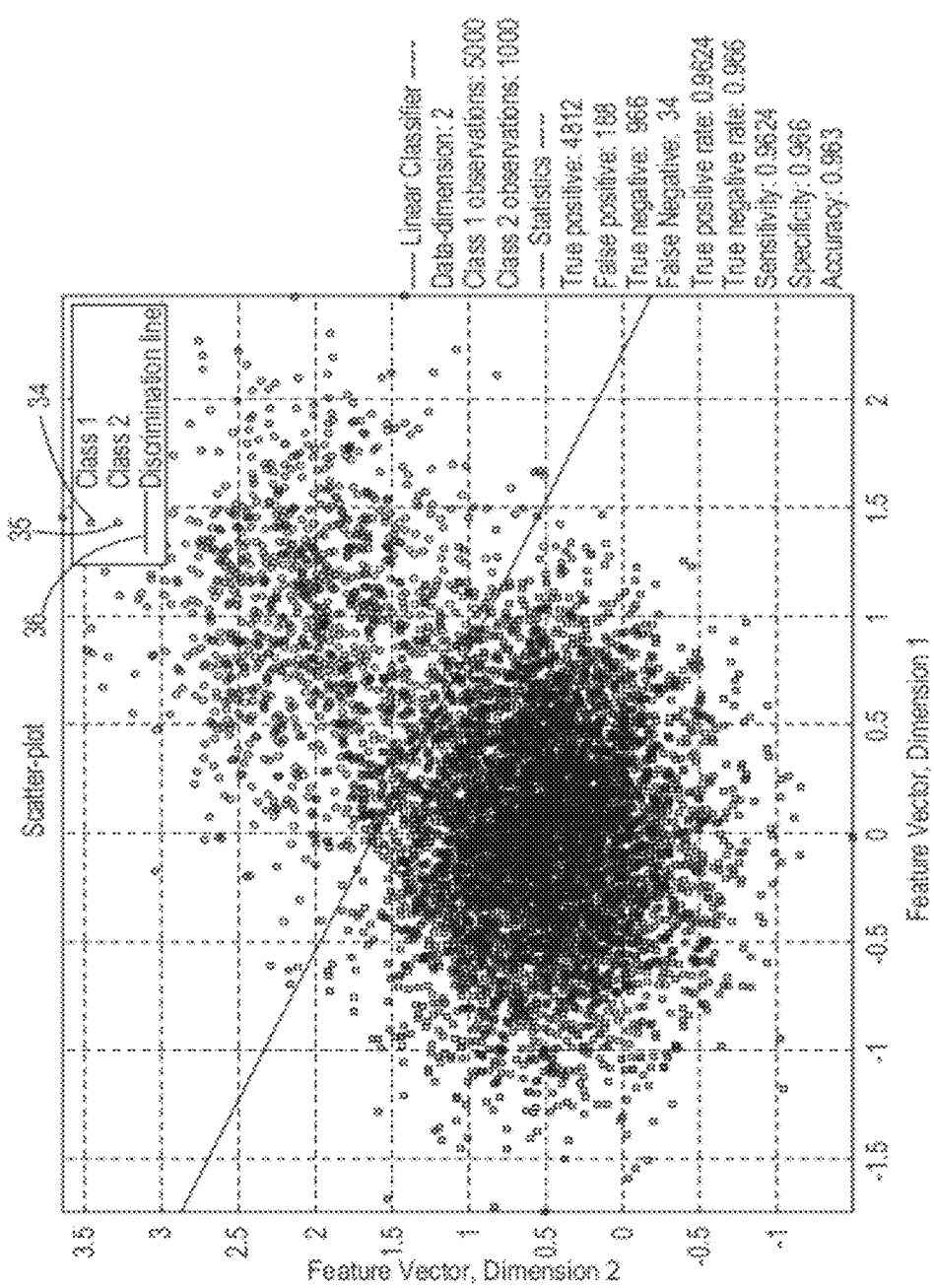

The invention will now be describe in greater detail based on non-limiting exemplary embodiments, and with reference to the drawings on which FIG. 1 depicts a head of a person with an EEG monitoring system according to an embodiment of the invention, FIG. 2 depicts a block diagram of the EEG monitoring system of FIG. 1, FIG. 3 depicts a block diagram an embodiment of the hypoglycaemia monitor and data logging blocks of FIG. 2, FIG. 4 depicts integrated event level over time compared to plasma glucose level in the blood of a patient, FIG. 5 depicts a histogram over event level versus time of day for a number of days, FIG. 6 depicts a circular buffer for storing successive feature vectors, and FIG. 7 is a scatter plot illustrating a simple classifier.

DETAILED DESCRIPTION OF THE DRAWINGS

FIG. 1 schematically shows the head 1 of a person carrying an EEG monitoring system 2 according to an embodiment of the invention. The EEG monitoring system 2 comprises an implant unit 3 for measuring EEG's. The implant unit 3 is located subcutaneously behind the ear 4 of a patient. The implant unit 3 comprises an electronics part 5 and a probe means 6 with at least two electrodes 12 (not visible in FIG. 1) for picking up electrical EEG signals from the brain of the patient. The electronics part 5 of the implant unit 3 comprises the necessary electronics means for sampling the EEG signals measured by the electrodes and transmitting them wirelessly to an external unit 7 forming part of the EEG monitoring system 2. Preferably, the energy supply to the implant unit 3 is received inductively from the external unit 7, so that the implant unit 3 has a long service life not constrained by battery power. This is advantageous as the replacement of a battery would necessitate a surgical procedure for replacement of the whole implant unit 3.

As can be seen, the external unit 7 may resemble a Behind-The-Ear hearing aid (BTE hearing aid), comprising a housing part 8, which in normal use is placed behind an ear 4 of the person carrying the EEG monitoring system 2, and an earplug 9. Like a BTE hearing aid, the housing part 8 is connected to the earplug 9 in the ear canal of the person via an intermediate connection 10. This could be a traditional sound tube leading to an earplug or an electrical cord leading to a Receiver In The Ear type earplug (RITE earplug). This allows the external unit 7 to give off messages, such as alarms or warnings, into the ear 4 of the person carrying the EEG monitoring system 2.

As indicated, the EEG monitoring system 2 may optionally include a peripheral device 11, which as will be explained later may comprise additional and possibly more energy consuming electronic storage space for data.

Turning now to FIG. 2 the internal details of the EGG monitoring system 2 are schematically shown. Starting with the implant unit 3, this comprises two electrodes 12 for measuring the electrical brain waves. Evidently, there may be more than two electrodes 12, but for ease of description and illustration only two are shown. The electrodes are connected to an analog front-end 13, amplifying the electrical signals from the electrodes 12 before they are sampled to form a digital data signal. A typical sampling rate would be 256 Hz, 256 Hz being a good compromise between the wish of keeping the energy consumption of the implant unit 3 low, and the frequencies actually measurable with an implant located subcutaneously outside the scull. The sampled data is fed to a channel encoder 14, which in turn provides an input to a wireless data transmitter 15. As can be seen, the wireless data transmitter 15 is preferably incorporated in the energy receiver, with which the energy supply is received from the external unit 7. Preferably the energy supply is received inductively using an implant unit coil 16, and the data trans-mission provided by varying the load on the implant unit coil 16. This load variation may readily be detected by sensing the load on a corresponding combined energy transmitter and data receiver 17 feeding an external unit coil 18.

In the external unit 7 the data received from the energy transmitter and data receiver 17 is provided to a channel decoder 19, reconstructing the digital data signal from the front end 13 in the implant unit 3, and providing the reconstructed digital data signal to a hypoglycaemia monitor 20. The hypoglycaemia monitor 20 and the functionality thereof will be described in greater detail below.

The hyperglycaemia monitor 20 delivers an output signal to the device operating controller 21, which in turn controls an audio generator 22 for generating an audio signal, such as a warning or an alarm to the speaker 23. As mentioned above the speaker 23 may be a part of a RITE earplug or it may be in communication with a passive earplug via a sound tube. The device operating controller also controls a data logging unit 24, which may be used to store information in a non-volatile memory 25 such as an EEPROM. As mentioned above information may also be transmitted to a peripheral device 11 having a data-logging reader 26 capable of receiving and reading the data and storing it in a suitable data storage 27, here termed flash data-logger, of larger capacity than available in the external unit 7, e.g. a flash memory. The peripheral device need not be a dedicated storage device, but may be a unit incorporating other functionalities too, e.g. a remote control unit.

FIG. 3 illustrate the hypoglycaemia monitor 20 broken down to four basic parts, namely a feature extractor 28, a classifier 29, an event integrator 30 and an alarm unit 31, as well as the data-logger 24 and the non-volatile memory 25. Furthermore, a real time clock 32 for keeping track of occurrence of events is shown. The input signal to the hypoglycaemia monitor 20 from the channel decoder 14 is essentially just a continuous bit-stream. In order to derive useful information, this bit-stream is first fed to a feature extractor 28 for extracting desired features. The feature extractor images the input signal in a feature vector FV in order to reduce the dimensions, the input signal having a higher dimension than the resulting feature vector FV.

As will be understood from the below description, such an extraction can be performed in many ways, that is to say the actual parameters forming the feature vector can be selected in many different ways. Parameters for a feature vector could be averaged FFT coefficients, power measurement for clinical bands, or the amplitude distribution in frequency bands, e.g. percentiles, median, skewness. Also trends could be used, i.e. whether a given band feature is increasing or declining.

One way of doing this is to subdivide the bit-stream into blocks, e.g. corresponding to the 256 Hz sampling rate. These blocks may be fed to an FFT processor with a suitable number of points e.g. 256 or 128. This will yield an output vector reflecting the energy distribution of the EEG signals over a corresponding number of frequency bands between 0 Hz and 256 Hz, i.e. over 128 bands, each with a width of 2 Hz, or over 256 bands, each with a width of 1 Hz, depending on the number of points of the FFT. For each block processed by the FFT, the FFT generates one output vector of the corresponding number of dimensions, i.e. a 128 or 256 dimensional vector. Of course the output of the FFT could be averaged over a number of successive blocks.

This itself merely constitutes a change of basis. The feature vector FV is really only achieved by further reducing the dimensions. One way of achieving this is by looking at the energy distribution between specific broader frequency bands, in particular the frequency bands known as clinical bands. The clinical bands are normally defined as 0-4 Hz (Delta), 4-7 Hz (Theta), 8-12 Hz (Alpha), 12-30 Hz (Beta) and 30-100+Hz (Gamma). However, for convenience slight deviations could be used in the feature vector, e.g. 0-4 Hz, 4-8 Hz, 8-16 Hz, 16-32 Hz and 32-256 Hz, the interval limits corresponding to multiples of 2. This would then yield a five dimensional feature vector FV, each dimension representing a momentary energy distribution in the different clinical bands of the EEG signal.

Successive feature vectors are stored at predetermined intervals, e.g. every 10 seconds, in a circular memory or buffer 33 of suitable length in the data logger 24, as illustrated in FIG. 6. The circular buffer 33 illustrated comprises N feature vector samples FV, where n indicates the time index for the sample. FV(n) is thus the feature vector FV sample at the current time, FV(n−1) is the previous feature vector sample, etc. For every update of the time index, e.g. every 10 seconds, as mentioned above, the oldest feature vector sample FV(n−N+1) is overwritten with the data of an new feature vector sample FV(n).

The classifier 29 monitors the feature vectors FV for predetermined patterns identifiable as signs of hypoglycaemia, e.g. by looking at the energy distribution between the clinical bands. The classifier may look at the RMS value of the energy in these clinical bands for patterns known to signal hypoglycaemia or imminent hypoglycaemia.

An example of such a classifier is illustrated by the scatter plot of FIG. 7, corresponding to a two dimensional classifier. Dimension 1, plotted along the abscissa, could be the energy in the Theta band and dimension 2, plotted along the ordinate, could be the energy in the Alpha band. The classifier outputs Class 1 if the energy in both the Alpha and the Theta band are low, corresponding to the dark coloured squares 34, and Class 2 if the energy in both the Alpha band and the Theta band are high, corresponding to the light coloured circles 35. The optimum classifier is defined by the fully drawn line 36.

The classifier is thus adapted to distinguish between two classes indicated by dark coloured squares 34 and light coloured circles 35. Observations above this line 36 are classified as belonging to Class 2, whereas observations below the line 36 are classified as belonging to Class 1, e.g. hypoglycaemia.

As can be seen from the illustrated example, no two dimensional classifier which fully separates the two classes exists. As indicated in the lower right-hand corner of FIG. 7, there are 5000 observations truly belonging to Class 1 and 1000 truly belonging to class 2. Herein 4812 of the 5000 observations belonging to Class 1 are correctly classified and the remaining 188 incorrectly classified. Conversely, 34 observations belonging to Class 2 are incorrectly identified as Class 1 observations.

Logging the feature vector FV, and storing it when an alarm is triggered based on the events classified, will allow subsequent analysis of the data, which in turn would allow the angle and level of the line 36 to be modified, i.e. the classifier to be trained, in order to reduce the future number of false positives or negatives. A reduction in false positives and false negatives will, in turn, lead to a higher number of correct alarms and less false alarms. Though being simple, a two dimensional classifier will not be sufficient for practical purposes in the context of the present invention, and is only to serve as an example.

Whereas a sampling frequency of 256 Hz may be suitable for sampling the EEG signals themselves, this frequency is far higher than the rate with which events need to be monitored, in order to detect developments in the signal pattern. The classifier thus would typically only perform its classification at longer intervals, e.g. once per second or 5 to 10 times per minute.

If such a pattern is detected, the classifier identifies an event, and an event signal is output to the event integrator 30. The event integrator 30 integrates the event signals over time, in order to produce an event level signal. The integration preferably has a decaying function, so that the event integrator only gives rise to a high event level in periods with a high frequency of events. In this respect it should be noted that integration in this context is to be understood broadly, including first and second order recursive integration, e.g. an AR-filter, and including leaky integrations and other integrations with a decaying function.

The event level signal is detected by the alarm unit 31, which via the device operating controller 21 triggers the audio generator 22 or gives off a warning or an alarm in the speaker 23 upon predetermined criteria. A simple but preferred criterion is an event level threshold, which when exceeded triggers the alarm or warning.

FIG. 4 shows an example of an event level signal over time for a test person and compared to actual measured values for the plasma glucose level in the blood of the test person over the same time period. An event level threshold of 0.6 is indicated. As mentioned above, a simple two dimensional classifier will hardly suffice for the purposes of this invention, and the example is based on a more complex classifier using 29 dimensions.

Apart from logging the feature vector in a circular buffer 33, it is also possible to log the actually sampled EEG signal, preferably also in a circular buffer. Also the time of occurrence of events could be logged using the real time clock 32.

Seizures, such as hypoglycaemic seizures and epileptic seizures, do not develop in identical ways with identical patterns in different persons. Logging information and detecting events greatly improves the possibilities for gaining experience and learning more about when and in what situations the person carrying the EEG monitoring system is at risk of a seizure, such as a hypoglycaemic seizure or an epileptic seizure, as well as for detecting the individual patterns. This, in turn, allows for individual adaptation of algorithms, e.g. the training of the classifier, or adjustment of the alarm threshold, both leading to fewer false alarms.

The present invention therefore allows information to be stored at suitable points in time. One such suitable point in time would be when an alarm or a warning is triggered. In such an event the raw sampled data from the EEG signal for e.g. the last 30 minutes leading up to the warning could be stored in the non-volatile memory 25. However, as storage space may be sparse it might be feasible to subject the sampled data from the EEG signal to a loss-less data compression before storage. An alternative, saving even more storage space, could be to store only the entire circular feature vector buffer 33 comprising the feature vector samples FV(n−N+1) to FV(n), as illustrated in FIG. 6. In both cases information giving a picture of the events leading up to the incident is saved for later scrutiny.

As indicated in FIG. 2 information from the data logger and/or the non-volatile memory may be read out to a peripheral device 11. This peripheral device 11 could be a device for processing the information to learn more, or it could be a larger but less energy efficient storage means, e.g. a flash memory or the like. This peripheral device 11 is not intended to be carried at all times. Rather, it is envisaged that it could be placed near the bed of the person carrying the EEG monitoring system according to an embodiment of the invention, and that data could be transferred thereto overnight while the person is asleep in his bed.

As an alternative to the alarm based storage of data, data could also be stored at regular intervals, e.g. every 15 minutes based on the real time clock 32, again depending on the amount of storage space available in the non-volatile memory 25.

In particular, it is in this respect preferred to save information about the event level. If the current event level is stored at regular intervals, e.g. every 15 minutes, it becomes possible to monitor the development of the person carrying the EEG monitoring device over a 24 hour period. Thus it may be possible to detect whether there are times during such a 24 hour period which are especially critical, and where the person carrying the EEG monitoring device could himself do something for his health, e.g. increase the intake of sugar or take his insulin.

This is in particular of interest if such data are accumulated over longer time periods such as months or even years.

FIG. 5 depicts a two dimensional histogram over event level versus time of day for a large number of days, and the greyscale indicates the height of the columns of the histogram. For each day in a longer period, each respective event level of the 96 time intervals has been added to the corresponding column of the histogram. A high intensity thus indicates that at this specific time a specific event level frequently occurs. It can readily be appreciated that about 16:00 the person carrying the EEG monitoring device very frequently has a very high event level. Likewise, the person usually has a low to moderate event level during the night. The histogram based on the logged data thus gives a clear indication that the person carrying the EEG monitoring device should be extra aware of hypoglycaemia in the late afternoon, and perhaps ought to take precautions by changing his daily rhythm of intake of sugar and insulin.

The full data of such a histogram could be stored in the non-volatile memory of the external unit 7. However, it would be preferred to store the data in the peripheral device, having more storage space, and possibly connected to a computer for computation and display of the histogram.

With the data logging described above, and storage of the logged data, in particular the event based storage, the person carrying the portable EEG monitoring system will not only be able to obtain an individually adapted alarm threshold and event classification, but also be able to obtain guiding information in terms of nutrition, use of insulin, and eating habits, and trough this learn the reaction patterns of his body.

The invention has mainly been described above with reference to a few embodiments. However, as is readily appreciated by a person skilled in the art, other embodiments than the ones disclosed above are equally possible within the scope of the invention, as defined by the appended patent claims.

We claim:

1. A portable EEG monitoring system, said system comprising:
   electrodes for measuring an EEG signal from a person carrying the EEG monitoring system,
   a signal processor adapted to receive, process and analyze at least a part of said EEG signal, wherein said signal processor comprises a feature extractor for extracting a feature vector from said EEG signal,
   a classifier adapted for monitoring said feature vector for identifying an event and outputting an event signal to an event integrator adapted to integrate event signals over time, in order to produce an event level signal,
   a data logger adapted to log data relating to said EEG signal, including the feature vector extracted from said EEG signal, and
   a memory for storing said data relating to said EEG signal;
   wherein said data logger includes a circular buffer for storing data over no more than a predetermined period of time, and said memory stores data logged in said data logger, including said feature vector, when said event level signal exceeds an event detection threshold.

2. The EEG monitoring system according to claim 1, wherein said classifier comprises an event classifier for detecting important events based on said EEG signal.

3. The EEG monitoring system according to claim 2, wherein said classifier detects an abnormal brain condition based on the detected important events, and initiates an alarm based on said detection of the abnormal brain condition.

4. The EEG monitoring system according to claim 1, wherein the data logger is adapted to log information about a number of events.

5. The EEG monitoring system according to claim 1, wherein the data logger is adapted to log the waveform of said EEG signal.

6. The EEG monitoring system according to claim 1, wherein said classifier comprises a multi-dimensional classifier.

7. The EEG monitoring system according to claim 6, wherein said classifier identifies the event as a function of a combination of a plurality of parameters.

8. The EEG monitoring system according to claim 6, wherein said event corresponds to hypoglycaemia.

9. The EEG monitoring system according to claim 1, wherein said classifier monitors said feature vector for patterns of signal characteristics indicative of an event of interest.

10. A portable EEG monitoring system, said system comprising:

electrodes for measuring an EEG signal from a person carrying the EEG monitoring system, a signal processor adapted to receive, process and analyze at least a part of said EEG signal, wherein said signal processor comprises a feature extractor for extracting a feature vector from said EEG signal, a classifier adapted for monitoring said feature vector for identifying an event and outputting an event signal to an event integrator adapted to integrate event signals over time, in order to produce an event level signal, wherein said classifier comprises an event classifier for detecting important events based on said EEG signal, a data logger adapted to log data relating to said EEG signal, including the feature vector extracted from said EEG signal, and a memory for storing said data relating to said EEG signal;

wherein said data logger includes a circular buffer for storing data over no more than a predetermined period of time, and said EEG monitoring system is configured to detect an abnormal brain condition when said event level signal exceeds an event detection threshold, and wherein said memory stores data logged in said data logger, including said feature vector, in response to said event level signal exceeding said event detection threshold.

11. A method for EEG monitoring using a portable EEG measuring system, said method comprising:

measuring an EEG signal from a person carrying the EEG monitoring system, receiving, processing and analyzing at least a part of said EEG signal using a signal processor, said signal processing comprising the extraction of a feature vector from said EEG signal using a feature extractor, monitoring said feature vector, identifying an event using a classifier and outputting an event signal to an event integrator and producing an event level signal by integrating event signals over time using said event integrator, logging data relating to said EEG signal using a data logger, including the feature vector extracted from said EEG signal, and storing said data relating to said EEG signal in a memory;

wherein said data logger includes a circular buffer for storing data over no more than a predetermined period of time, and said memory stores data logged in said data logger, including said feature vector, when said event level signal exceeds an event detection threshold.

12. The method according to claim 11, wherein important events are detected based on said EEG signal, using an event classifier.

13. The method according to claim 12, wherein an awareness condition is detected based on the important events, and an alarm initiated based on said detection of the awareness condition.

14. The method according to claim 11, wherein information about a number of events is logged using said data logger.

15. The method according to claim 11, wherein the waveform of said EEG signal is logged in said data logger.

16. The method according to claim 11, wherein said classifier comprises a multi-dimensional classifier.

17. The method according to claim 16, wherein said classifier identifies the event as a function of a combination of a plurality of parameters.

18. The method according to claim 11, wherein said classifier monitors said feature vector for patterns of signal characteristics indicative of an event of interest.

19. The method according to claim 16, wherein said event corresponds to hypoglycaemia.

20. A method for EEG monitoring using a portable EEG measuring system, said method comprising:

measuring an EEG signal from a person carrying the EEG monitoring system, receiving, processing and analyzing at least a part of said EEG signal using a signal processor, said signal processing comprising the extraction of a feature vector from said EEG signal using a feature extractor, monitoring said feature vector, identifying an event using a classifier and outputting an event signal to an event integrator and producing an event level signal by integrating event signals over time using said event integrator, logging data relating to said EEG signal using a data logger, including the feature vector extracted from said EEG signal, and storing said data relating to said EEG signal in a memory;

wherein important events are detected based on said EEG signal, using an event classifier;

wherein an awareness condition is detected based on the important events, and an alarm initiated based on said detection of the awareness condition, wherein said EEG monitoring system is configured to detect said awareness condition when said event level signal exceeds an event detection threshold; and wherein said data logger includes a circular buffer for storing data over no more than a predetermined period of time, and said memory stores data logged in said data logger, including said feature vector, in response to said event level signal exceeding said event detection threshold indicating detection of said awareness condition.

* * * * *